United States Patent [19]

Honkanen et al.

[11] Patent Number: 5,382,699
[45] Date of Patent: Jan. 17, 1995

[54] METHOD FOR THE PREPARATION OF 3,4-DIHYDROXY-5-NITROBENZALDEHYDE

[75] Inventors: Erkki Honkanen, Espoo; Stig Lindholm, Helsinki, both of Finland

[73] Assignee: Orion-yhtymä Oy, Espoo, Finland

[21] Appl. No.: 162,198

[22] PCT Filed: Jun. 18, 1992

[86] PCT No.: PCT/FI92/00192

§ 371 Date: Jan. 6, 1994

§ 102(e) Date: Jan. 6, 1994

[87] PCT Pub. No.: WO93/00323

PCT Pub. Date: Jan. 7, 1993

[30] Foreign Application Priority Data

Jun. 20, 1991 [GB] United Kingdom ............... 9113431

[51] Int. Cl.$^6$ ............................................. C07C 45/00
[52] U.S. Cl. .................................... 568/436; 568/426
[58] Field of Search ............................... 568/436, 426

[56] References Cited

U.S. PATENT DOCUMENTS

| | | | |
|---|---|---|---|
| 4,009,210 | 2/1977 | Cahoy | 568/436 |
| 4,963,590 | 10/1990 | Bäckström et al. | 514/678 |
| 5,112,861 | 5/1992 | Bäckström et al. | 514/520 |
| 5,135,950 | 8/1992 | Pippuri et al. | 514/521 |

FOREIGN PATENT DOCUMENTS 0237929 9/1987 European Pat. Off. .
967605 8/1964 United Kingdom .

OTHER PUBLICATIONS

"Selective Dealkylation of Activated Aromatic Ethers", by Christer Hansson and Börje Wickberg, *Synthesis*, Nos. 3, pp. 191 to 192 (1976).

"Demethylation of Aryl Methyl Ethers With Tioethoxide Ion in Dimethyl Formamide" by G. I. Feutrill and R. N. Mirrington, Tetrahedron Letters No. 16, pp. 1327 to 1328, (1970).

*Primary Examiner*—Werren B. Lone
*Attorney, Agent, or Firm*—Burns, Doane, Swecker & Mathis

[57] ABSTRACT

A method for the preparation of 3,4-dihydroxy-5-nitrobenzaldehyde by reacting 4-hydroxy-3-methoxy-5-nitrobenzaldehyde with a strong nucleophilic agent which may be created by reacting an aromatic mercapto compound with a strong organic or inorganic alkali metal base such as lithium hydroxide. The reaction is performed at elevated temperatures using an aprotic polar solvent. It is preferably carried out in an inert atmosphere.

6 Claims, No Drawings

METHOD FOR THE PREPARATION OF 3,4-DIHYDROXY-5-NITROBENZALDEHYDE

The invention relates to a new method for the preparation of 3,4-dihydroxy-5-nitrobenzaldehyde, which is an intermediate in the synthesis of several pharmaceutically important catechol compounds.

GB-A-2200109 and EP 237929 describe a method for the preparation of 3,4-dihydroxy-5-nitrobenzaldehyde, in which method 4-hydroxy-3-methoxy-5-nitrobenzaldehyde is refluxed in concentrated hydrobromic acid. This method has many disadvantages which make it industrially inapplicable. For example, hydrobromic acid causes serious corrosion problems and results in the formation of the by-product 2-bromo-3,4-dihydroxy-5-nitrobenzaldehyde and dark coloured decomposition products which both interfere with the purification of the desired 3,4-dihydroxy-5-nitrobenzaldehyde. The emission of the toxic gaseous by-product methyl bromide is also a serious problem.

It has now been surprisingly found that the above disadvantages may be avoided if the dealkylation reaction is performed using a strong nucleophilic reagent. Preferably, the nucleophile is thiolate anion of an aromatic mercapto compound such as thiophenol, 2-, 3- or 4-aminothiophenol, 2-, 3- or 4-thiocresol or 1- or 2-thionaphthol or 2-mercaptobenzothiazole. The thiolate anion is preferably created with the aid of a strong organic or inorganic base such as an alkali metal hydroxide, hydride or amide. Especially preferable are the lithium bases.

It is advisable to carry out the reaction in an inert atmosphere, thus preventing the formation of disulphide impurities. The reaction is preferably performed in an aprotic polar solvent, such as 1-methyl-2-pyrrolidinone, N,N-dimethylformamide or N,N-dimethylacetamide under reduced or normal pressure at elevated temperature in the range of about 80° to 160°, most preferably about 130° C.

The reaction is very suitable for industrial production because the reagents are readily available, cheap, non-corrosive and easily handled. The solvent used can be easily recirculated and there is no emission of toxic gases.

Hansson and Wickberg (Synthesis, No. 3, 1976, 192—192) handles with the selective dealkylation of aromatic ethers. Unlike in the present invention wherein the methyl group is in meta position as counted from the two electronegative groups (formyl and nitro) the article of Hansson and Wickberg describes reactions wherein the demethylation is selective in the para and especially in the orto position. Feutrill and Mirrington (Tetrahedron Letters, No 16, 1970, 1327–28) describes the demethylation of 4-bromo-3-methyl-anisole wherein the methoxy group is also in the para position.

EXAMPLE 1

20 g of 4-hydroxy-3-methoxy-5-nitrobenzaldehyde, 5.4 g of lithium hydroxide, 12 ml of thiophenol and 40 ml of NMP (1-methyl-2-pyrrolidinone) were mixed for two hours at 130° C. under nitrogen atmosphere. The mixture was cooled to 90° C. and 125 ml of water, 40 ml of heptane and 30 ml of strong hydrochlorid acid was added. The mixture was stirred overnight at room temperature, kept for two hours at 0° C., filtered, washed with 20 ml of cold water and dried. Yield 16.52 g (88.9%), m.p. 135°–137° C.

EXAMPLE 2

15 g of 4-hydroxy-3-methoxy-5-nitrobenzaldehyde, 4.1 g of lithium hydroxide, 9 ml of thiophenol and 25 ml of NMP were mixed for two hours at 130° C. under nitrogen atmosphere. The mixture was cooled to 100° C. and 50 ml of glacial acetic acid and 30 ml of concentrated hydrochloric acid were added. The mixture was stirred overnight at room temperature, kept for two hours at 0° C., filtered, washed with 20 ml of cold water and dried. Yield 11.38 g (81.7%), m.p. 135°–137° C.

EXAMPLE 3

15 g of 4-hydroxy-3-methoxy-5-nitrobenzaldehyde, 3.7 g of lithium hydroxide, 13 g of 2-mercaptobenzothiazole, 40 ml of NMP and 30 ml of toluene were refluxed with water separation for 20 hours under nitrogen atmosphere. The mixture was cooled to 80° C. and 150 ml of water and 20 ml of toluene were added. After stirring for half an hour the phases were separated and the toluene phase discarded. To the water phase 45 ml of concentrated hydrochloric acid was added. The mixture was stirred overnight at room temperature, kept for two hours at 0° C., filtered, washed with 20 ml of cold water and dried. Yield 12.64 g (90.7%), m.p. 135°–137° C.

EXAMPLE 4

150 g of 4-hydroxy-3-methoxy-5-nitrobenzaldehyde, 280 ml of NMP, 39 g of lithium hydroxide and 90 ml of thiophenol were kept at 130° C. for three hours under reduced pressure and the distillate was collected. The mixture was cooled to 100° C., the pressure normalized and 1000 ml of hot water and 250 ml of concentrated hydrochloric acid were added. The mixture was stirred overnight at room temperature, kept for two hours at 0° C., filtered, washed with 200 ml of cold water and dried. Yield 135 g (96.9%), m.p. 135°–137° C.

We claim:

1. A method for the preparation of 3,4-dihydroxy-5-nitrobenzaldehyde comprising the reaction of 4-hydroxy-3-methoxy-5-nitrobenzaldehyde in an aprotic polar solvent at the temperature from 80° to 160° C. with the lithium salt of an aromatic mercapto compound.

2. The method according to claim 1, wherein the aromatic mercapto compound is 2-mercaptobenzothiazole.

3. The method according to claim 1, wherein the aromatic mercapto compound is thiophenol.

4. The method according to claim 1, wherein it is performed in an inert atmosphere.

5. The method according to claim 1, wherein the aprotic polar solvent is 1-methyl-2-pyrrolidinone.

6. The method according to claim 1, wherein it is performed at the temperature of about 130° C.

* * * * *